(12) United States Patent
Ge et al.

(10) Patent No.: US 8,591,931 B2
(45) Date of Patent: Nov. 26, 2013

(54) CORONARY STENT WITH ASYMMETRIC DRUG RELEASING CONTROLLED COATING

(75) Inventors: Junbo Ge, Shandong (CN); Shenguo Wang, Shandong (CN); Jianzhong Bei, Shandong (CN); Haijun Zhang, Shandong (CN); Xiangfei Wang, Shandong (CN); Xiaoxin Shang, Shandong (CN); Haihong Guo, Shandong (CN)

(73) Assignee: Shangdong Intech Medical Technology Co., Ltd, Shandong (CN)

( * ) Notice: Subject to any disclaimer, the term of this patent is extended or adjusted under 35 U.S.C. 154(b) by 0 days.

(21) Appl. No.: 12/527,251

(22) PCT Filed: Feb. 14, 2007

(86) PCT No.: PCT/CN2007/000542
§ 371 (c)(1),
(2), (4) Date: Feb. 9, 2010

(87) PCT Pub. No.: WO2008/098418
PCT Pub. Date: Aug. 21, 2008

(65) Prior Publication Data
US 2010/0168842 A1 Jul. 1, 2010

(51) Int. Cl.
*A61F 2/82* (2013.01)
*A61L 33/04* (2006.01)

(52) U.S. Cl.
USPC .................. 424/423; 623/1.42; 427/2.25

(58) Field of Classification Search
None
See application file for complete search history.

(56) References Cited

U.S. PATENT DOCUMENTS

| | | | |
|---|---|---|---|
| 5,464,650 A | 11/1995 | Berg et al. | |
| 5,624,411 A | 4/1997 | Tuch | |
| 5,679,400 A | 10/1997 | Tuch | |
| 5,776,184 A | 7/1998 | Tuch | |
| 5,837,008 A | 11/1998 | Berg et al. | |
| 6,997,949 B2 | 2/2006 | Tuch | |
| 2002/0138048 A1 | 9/2002 | Tuch | |
| 2003/0068355 A1* | 4/2003 | Shanley et al. | 424/426 |
| 2005/0075714 A1* | 4/2005 | Cheng et al. | 623/1.11 |
| 2005/0281883 A1* | 12/2005 | Daniloff et al. | 424/489 |
| 2006/0002968 A1* | 1/2006 | Stewart et al. | 424/423 |
| 2006/0085064 A1 | 4/2006 | Tuch | |
| 2006/0161242 A1 | 7/2006 | Lee et al. | |

OTHER PUBLICATIONS

International Search Report for PCT/CN2007/000542 dated Nov. 22, 2007.

* cited by examiner

*Primary Examiner* — Robert A Wax
*Assistant Examiner* — H. Sarah Park
(74) *Attorney, Agent, or Firm* — Turocy & Watson, LLP

(57) ABSTRACT

A coronary stent is provided with asymmetric drug releasing controlled coating used in interventional therapy of coronary disease, containing a bare stent and a coating consisting of drug and carrier, the coating is coated onto the outer wall surface of the bare stent, and is multi-layered. The drug concentration in the coating increases in sequence from the outer layer to the inner layer. The drugs used in different layers of the coating may be identical or different, and particularly may be one or more selected from taxol, rapamycin, heparin, docetaxel and a combination thereof. The carrier may be a random (lactide-glycolide) copolymer having a molecular weight of 50,000-200,000. The drug-coated stent of the present invention employs highly effective drugs, enabling a thinnest coating and reducing the vascular irritation. The drug release is regulated by altering the coating manner so as to satisfy the clinical requirement for controlled drug release. The employed asymmetric coating promotes regenerative repairing of vascular endothelium. The present invention is a drug-coated coronary stent with reasonable design, with the coating capable of effectively preventing vascular restenosis and reducing occurrence of late thrombosis.

3 Claims, No Drawings

CORONARY STENT WITH ASYMMETRIC DRUG RELEASING CONTROLLED COATING

TECHNICAL FIELD

The present invention relates to a medical device, and particularly relates to a stent having an asymmetric drug coating and drug releasing controlled coating, which is employed in the interventional therapy of coronary heart diseases.

BACKGROUND

Coronary heart disease is a major threat to human health. More than 2.4 million people received cardiac interventional therapy in the year of 2005. An incidence of coronary heart disease is very high in China, with more than one million individuals afflicted with this disease per year. However, only 100,000 patients in China have access to interventional therapies due to economic and technical limitations. Drug-coated stents can reduce the long-term restenosis rate from 20-50% to 5-10%, and are considered a revolutionary breakthrough in therapy in the modern medical development. The drug-coated stents have been applied in more than 80% of the interventional therapy cases. For example, Chinese Patent No. 02100011.5 discloses a drug coating for coronary stent preventing the vascular restenosis. Such a coating can be obtained by adding a drug of paclitaxel (Taxol®) into a solution of drug carrier comprised of aliphatic polymer of lactone and copolymers thereof, and then coating the above obtained mixture onto the surface of the coronary stent through a spray coating or dipping coating process. Such stents with a drug coating may provide simple and feasible solutions for preventing the vascular restenosis. However, at a conference of the World Heart Association (WCC) and the European Heart Association (ESC) in Sep. 2-6, 2006, at Barcelona, Spain, it was reported that the late infarction rate of a drug coated stent was slightly higher than that of a bare stent. Such a statistical result revealed new challenges to the drug coated stent. Therefore, for the purpose of satisfying a higher demand for eliminating early restenosis and late infarction in clinical practice, further consideration must be given to the followings: 1. the dose and timing of drug release must be adjusted in accordance with clinical demands; 2. the coating of the stent serving as a drug carrier should be removed as soon as possible after the drug has been completely released; 3. highly effective drugs are employed so as to reduce the drug dosage and the coating thickness; 4. the drug coating of the stent should not affect repairing of vascular endothelium so that a thrombosis can be avoided.

SUMMARY OF THE INVENTION

The aim of the present invention is to provide a coronary stent with asymmetric drug releasing controlled coating, which can meet a higher clinical requirement, and a method for producing the same.

The present invention provides a coronary stent with asymmetric drug releasing controlled coating, comprising a bare stent and a coating consisting of drug and carrier. The coating is coated onto the outer wall surface of the bare stent, and the coating is multi-layered. The drug concentration of the coating increases in sequence from the outer layer to the inner layer.

In the stent according to the present invention, the carrier used in the coating is a random (lactide-glycolide) copolymer having a molecular weight of 50,000-200,000, wherein the content of polylactide is 25-80 mol %.

In the stent according to the present invention, the drug used in the coating is one or more selected from paclitaxel, rapamycin, heparin, docetaxel and a combination thereof.

In the stent according to the present invention, the drug used in the coating is docetaxel, or a combination of docetaxel and one or more selected from taxol, rapamycin and heparin.

In the stent according to the present invention, the coating has a drug concentration of 1-50% in its inner layer, and a drug concentration of 0-50% in its outer layer.

In the stent according to the present invention, the coating has an active drug concentration increasing gradually from the outer layer to the inner layer.

In the stent according to the present invention, the stent is made of stainless steel, nickel-titanium alloy, or a metal with titanium coated on its surface.

In the stent according to the present invention, the drugs used in different layers of the coating may be identical or different.

The invention also provides a method for producing a coronary stent with asymmetric drug releasing controlled coating, comprising coating a multi-layered coating containing drug and carrier onto the outer wall surface of a bare stent.

Particularly, the method comprises the acts of: dissolving a drug carrier into a solvent homogeneously, dividing the obtained solution into several portions and then adding the drug separately, stirring the obtained mixtures until the drug is dissolved, filtering the mixtures to give different drug solutions, coating the different drug solutions onto the outer wall surface of a bare stent by layers, volatilizing the solvent in the air and then removing the solvent in vacuum at room temperature for 48 hours, and sterilizing with ethylene oxide.

In the method according to the present invention, the solvent is tetrahydrofuran, acetone, dichloromethane, or chloroform.

With the above technical solutions, the stent of the present invention has a structure of asymmetric drug releasing controlled coating in favor of growth of endothelial cells and recovery of vascular endothelium. The drug carrier is continuously degraded and absorbed during releasing of the drug, and may disappear immediately after the drug is completely released. Therefore, a vascular irritation caused by the coating of the stent may be avoided in the later period. The use of highly effective drugs may reduce the drug dosage and the coating thickness so as to decrease the vascular irritation at the early stage. A double-layered or multi-layered drug-coating technique with layers having different drug releasing rate is employed in order to adjust the dose and timing of drug release.

EMBODIMENT OF THE INVENTION

In general, the present invention provides a coronary stent with asymmetric drug releasing controlled coating, comprising three elements of a bare stent, a drug, and a drug carrier, wherein the drug and the drug carrier are formulated together as a coating for coating the bare stent. In order to satisfy a higher demand in clinical practices, further research has been conducted in aspects of ingredients, dose and concentration of the drug, ingredient and content of the carrier, and the coating process.

The drug coating used in the present invention will be discussed below.

Drug Ingredients:

According to the previous reports, drugs of paclitaxel (the Chinese patent CN021 000 11.5), rapamycin, heparin or the like can be used in the coating of the stent. These drugs are effective in preventing the vascular system from restenosis. However, in the situation that these drugs are coated onto the stent in combination with carrier materials in a coating, the drug dose and the release timing and rate of the drug cannot satisfy the clinical demands sufficiently. Therefore, the way of using these known drugs, including choice of carrier materials and coating process for coating the drug, is further studied in the present invention in order to satisfy higher clinical demands.

On the other hand, the present invention employs a new drug of docetaxel for coating the stent. Docetaxel is a semi-synthetic paclitaxel derivative, and can accelerate polymerization of tubulin to microtubule, and delay depolymerization of microtubule. This can lead to formation of very stable nonfunctional microtubule bundles, and thereby destroy the mitosis and cell proliferation. Docetaxel used in the coating of the stent is advantageous due to its features of small dosage and significant efficacy. Therefore, the use of docetaxel can reduce the dose of the drug as well as the amount of the carrier, thus reducing side effects significantly. The concentration of docetaxel used in the drug coating of the stent can be in a range of $0.01-1 /!g/mm^2$.

Moreover, combination of docetaxel with other known drugs has been studied in connection with coating processes in the present invention, resulting in good results.

Drug Carrier:

First, material as the carrier can be a polymer material which may disappear relatively quickly after the drug is completely released. Second, material as the carrier can be highly biocompatible and vascular inirratative. Third, material as the carrier can be capable of controlling the timing and rate of drug release. Fourth, the degradation products of the drug carrier can have minimal or no side effects to human body.

Biodegradable aliphatic polylactones can be selected as the drug carrier of the coating of the stent according to the present invention. Since each of polylactide acid (PLA), polyglycolic acid (PGA) and polycaprolactone (PCL) are biodegradable polymers approved to be used in vivo, they are non-toxic and highly biocompatible, and have excellent physical and chemical properties. These materials may be copolymerized. The degradation rate and physical and chemical properties of the copolymer can be adjusted by adjusting the components, ingredients, molecular weight and the distribution of the molecular weight of the copolymer, and thus release rate of drugs is controlled.

According to clinical studies, occurrence of early stage vascular restenosis is the most frequent in the time periods from 7 hours to 1 week, and from 2 or 3 months to 6 months after implantation of the stent. Therefore, the drug in the coating of the stent is preferably released approximately during these periods. The drug release is closely related to components of material as the carrier. In the present invention, depending upon the influence of physical and chemical properties and the degradation rate of different aliphatic polylactones on the drug release, a random (lactide-glycolide) copolymer (PLGA) having a molecular weight of 50,000-200,000 can be selected as material of the carrier, wherein the content of polylactide is 25-80 mol %.

Coating Processes:

In the present invention, the drug and drug carrier are formulated into a drug solution for coating. Then, the drug solution is coated onto the outer wall surface of the stent through a spray coating or dipping coating process In the present invention, an asymmetric coating process is employed. In this process, the outer wall of the stent being contacted with the vascular wall is coated, while the inner wall of the stent being contacted with the blood is not coated. Therefore, the present invention can realize the aim of reducing inhibition of endothelial cells caused by drugs which is favorable to regeneration of the vascular endothelium.

Another advantageous feature of the coating employed in the present invention is a double-layered or multi-layered coating process. By altering the drug concentration and drug species in respective layers of the coating in combination with species and properties of materials as the carrier, the present invention can realize the aim of controlling the timing and rate of the drug release.

Particularly, the outermost layer of the multi-layered coating has a relatively lower drug concentration, or is free of drug, in order to delay or decrease the drug release. Meanwhile, the inner layer(s) of the coating have a relatively higher drug concentration(s), so that drugs in the inner layer(s) can be released in large quantity after the drug in the outer layer has been essentially released and the material as carrier has been degraded. By modulating the drug concentration in different layers, the thickness of the layer and/or coating, and the category and performance of materials as the carrier, the drug in the coating of the present invention may be released in a controllable way, and the activity of the drug may be adjusted, so as to satisfy the clinical demand of avoiding vascular restenosis.

In particular coating operations, a technique of coating at one time a thin layer of highly active drug for each respective layer in the coating is employed in the present invention. Therefore, the present invention can realize the aim of decreasing vascular irritation caused by the coating carrier, reducing the amount of used carrier as much as possible, and thereby avoiding early vascular restenosis.

The present invention will be described below in more details by reference to Examples.

Example 1:

A random (lactide-glycolide) copolymer of 2.10 g (PLGA, molecular weight: 100,000, molar ratio of lactide/glycolide=70/30) was dissolved in acetone (0.5 L). Two thirds of the solution was taken, into which docetaxel (0.46 g) was added. A docetaxel (0.12 g) was added into the rest one third of the solution. These two solutions were stirred, separately, until the drug was dissolved, and then were filtered separately, to give a solution No. 1 and a solution No. 2.

The solution No. 1 was spray coated at one time onto the outer wall surface of a stent made of stainless steel (3.16 L, 3.0×20 mm). The solvent was volatilized in the air. Subsequently, the solution No. 2 was spray coated onto the outer wall surface of the stent, and the solvent was volatilized in the air. Next, the solvent was removed in vacuum at the room temperature for 48 hours, to give the coated stent of this example.

The stent of this example used 180 μg of carrier material. The docetaxel content in the outer layer of the coating was 10 μg, and the docetaxel content in the inner layer of the coating was 40 μg.

Example 2:

A drug-coated stent was prepared in the same manner as in Example 1, with the exception that 137 μg of carrier material (PLGA, molecular weight: 120,000, molar ratio of lactide/ glycolide=60/40) was used. The docetaxel content in the outer layer of the coating was 8 μg, and the docetaxel content in the inner layer of the coating was 30 μg.

Example 3:

A drug-coated stent was prepared in the same manner as in Example 1, with the exception that 193 μg of carrier material (PLGA, molecular weight: 50,000, molar ratio of lactide/glycolide=80/20) was used. The docetaxel content in the outer layer of the coating was 15 μg, and the docetaxel content in the inner layer of the coating was 45 μg.

Example 4:

A drug-coated stent was prepared in the same manner as in Example 1, with the exception that 234 μg of carrier material (PLGA, molecular weight: 200,000, molar ratio of lactide/glycolide=50/50) was used, and a drug of paclitaxel was used in the outer layer of the coating. The taxol content in the outer layer of the coating was 25 μg, and the docetaxel content in the inner layer of the coating was 40 μg.

Example 5:

A drug-coated stent was prepared in the same manner as in Example 1, with the exception that 283 μg of carrier material (PLGA, molecular weight: 80,000, molar ratio of lactide/glycolide=75/25) was used, and the coating was triple-layered, wherein the outer layer of the coating used docetaxel in a content of 15 μg, the middle layer of the coating used a drug of Rapamycin in a content of 50 μg. The docetaxel content in the inner layer of the coating was 20 g.

Example 6:

A drug-coated stent was prepared in the same manner as in Example 1, with the exception that 212 μg of carrier material (PLGA, molecular weight: 200,000, molar ratio of lactide/glycolide=25/75) was used. The coating was double-layered, wherein the outer layer of the coating used a drug of paclitaxel in a content of 25 μg. The paclitaxel taxol content in the inner layer of the coating was 85 μg.

Example 7:

A drug-coated stent was prepared in the same manner as in Example 1, with the exception that the outer layer of the coating is a PLGA (molar ratio of lactide/glycolide=50/50, molecular weight: 150,000) free of drug, the middle layer of the coating is a PLGA (molar ratio of lactide/glycolide=70/30, molecular weight: 100,000) containing docetaxel of 55 μg, and the inner layer of the coating is a PLGA (molar ratio of lactide/glycolide=80/20, molecular weight: 200,000) containing paclitaxel of 25 μg.

Example 8:

A random (lactide-glycolide) copolymer of 2.10 g (PLGA, molecular weight: 100,000, molar ratio of lactide/glycolide=70/30) was dissolved in acetone (0.5 L). Two thirds of the solution was taken, into which paclitaxel (0.46 g) was added. A paclitaxel (0.12 g) was added into the rest one third of the solution. These two solutions were stirred, separately, until the drug was dissolved, and then were filtered separately, to give a solution No. 1 and a solution No. 2.

The solution No. 1 was spray coated at one time onto the outer wall surface of a stent made of stainless steel (3.16 L, 3.0×20 mm). The solvent was volatilized in the air. Subsequently, the solution No. 2 was spray coated onto the outer wall surface of the stent, and the solvent was volatilized in the air. Next, the solvent was removed in vacuum at the room temperature for 48 hours, to give the coated stent of this example.

393 μg of carrier material (PLGA, molecular weight: 100,000, molar ratio of lactide/glycolide=70/30) was used in this example. The paclitaxel content in the outer layer of the coating was 31 μg, and the paclitaxel content in the inner layer of the coating was 70 μg.

Effect Tests:

1. Stent Implantation

The experimental animals were male miniature pigs, male whose weight ranges from 20 kg to 30 kg. The operation method is the same as that of human operations. After a general anesthesia, femoral arteriotomy was applied to the pig. A 7r catheter sheaths was inserted into the femoral artery. The catheter was delivered to the left circumflex ostia through the femoral artery. A guide wire is delivered into the left circumflex. After being sterilized by ethylene oxide, the stents prepared in each of Examples of the present invention and a control stent were installed in the balloon catheter and delivered to midportion of left circumflex. The control stent was the stent prepared in Example 1 of the Chinese patent No. 02100011.5. (carrier material: 2500 μg GLPA, molar of lactide/glycolide=50/50, 50 μg paclitaxel).

2. Minimum Lumen Diameter

An Angiography was applied to the parts of the experimental pigs implanted with the stent, respectively, at 4 weeks, 8 weeks and 12 weeks after implantation of stents. Particularly, after local disinfection, certain parts of pigs' bodies were incised so that femoral artery was exposed. The arterial sheath and coronary diagnosis catheter were inserted into the femoral artery, and were delivered to the coronary ostia through aorta. Coronary angiography was applied with DSA, and the lumen diameter of the blood vessel at the narrowest part was measured and recorded as the minimum lumen diameter.

3. Drug Release Rate

Sampling and Detection: The drug release experiment was carried out at 37° C. after the stent was immersed into 5 ml of buffer (pH 7.2). The stents were taken out at 1 week, 2 weeks, and 12 week, respectively, after immersion, washed with distilled water, and then were placed into the 10 ml colorimetric tubes containing 40% methanol. After oscillating (120 times/min) and extracting for 5 minutes, the drug content in the solution was determined by High-performance liquid chromatography (HPLC). The result was labeled as residual amount of drug. Calculation was conducted based on the formula below:

Drug release rate=(coating amount of drug−residual amount of drug)/coating amount of drug 4. Weight Loss Rate of Polymer Degradation A dried bare stent weighed $M_0$ was coated with polymer solution free of drugs. After the solvent has volatized and weight was constant, the stent weighed $M_1$. The stent was immersed into 5 ml buffer (ph 7.2), and then conducted a degradation test at 37° C. At 4 weeks, 8 week, and 12 weeks after immersion, the stent was taken out, washed by the distilled water, and then dried to constant weight of $M_2$.

Weight loss rate of polymer degradation (%)=$(M_1-M_2)/(M_1-M_0) \times 100$

5. Average Area of Vascular Intimal Hyperplasia

After the angiography was applied successively at 4 weeks, 8 weeks and 12 weeks after implantation of the stent, the animals were sacrificed. Coronary artery implanted with a stent was taken out. After formalin fixation, hard tissue embedded pathological section was performed. The sections were observed by an ordinary microscope, and a computer image analysis was applied. The average area of vascular intimal hyperplasia was calculated.

The test results are shown in Table 1 shown

TABLE 1

Effect test results

| Results | Minimum lumen diameter | | | Drug release rate | | | | Weight loss rate of polymer degradation | | | Average area of vascular intimal hyperplasia | | |
| --- | --- | --- | --- | --- | --- | --- | --- | --- | --- | --- | --- | --- | --- |
| | 4 weeks | 8 weeks | 12 weeks | 1 week | 2 weeks | 4 weeks | 12 weeks | 4 weeks | 8 weeks | 12 weeks | 4 weeks | 8 weeks | 12 weeks |
| Example 1 | 2.73 | 2.70 | 2.66 | 14.4 | 45.6 | 87.2 | 97.8 | 35 | 70 | 90 | 600 | 1000 | 1800 |
| Example 2 | 2.70 | 2.65 | 2.61 | 25.6 | 50.5 | 90.9 | 98.0 | 30 | 85 | 92 | 700 | 1100 | 1700 |
| Example 3 | 2.76 | 2.64 | 2.59 | 18.7 | 48.0 | 90.0 | 81.5 | 30 | 75 | 90 | 650 | 120 | 1700 |
| Example 4 | 2.75 | 2.63 | 2.58 | 30.2 | 58.0 | 92.0 | 98.0 | 55 | 80 | 99 | 650 | 1100 | 1800 |
| Example 5 | 2.74 | 2.63 | 2.60 | 16.6 | 48.6 | 80.0 | 92.0 | 50 | 75 | 93 | 650 | 1100 | 1600 |
| Example 6 | 2.80 | 2.65 | 2.59 | 25.8 | 51.0 | 91.0 | 98.0 | 50 | 75 | 92 | 550 | 1050 | 1700 |
| Example 7 | 2.76 | 2.74 | 2.68 | 10.3 | 50.6 | 75.2 | 90.8 | 40 | 85 | 99 | 650 | 1100 | 1500 |
| Example 8 | 2.70 | 2.67 | 2.60 | 14.3 | 45.7 | 87.0 | 97.9 | 45 | 80 | 90 | 700 | 1200 | 1900 |
| Control Example | 2.86 | 2.50 | 2.30 | 80.7 | 90.5 | 99.2 | — | 35 | 70 | 99 | 500 | 1800 | 3000 |

The above test results indicate that, in comparison with the control stent, the stent of the Examples of the present invention provide a drug release having a first releasing climax from at 1-2 weeks, and a second releasing climax at 2-4 weeks, and releases the drug steadily after 4 weeks. It can be seen that the release cycle of drugs in the stent can be effectively regulated by the design of the present invention, satisfying the clinical demands greatly.

By comparing the data of Examples 1 and 8, it can be seen that use of docetaxel can reduce the dose of the drug as well as the amount of the carrier. In comparison with paclitaxel, use of docetaxel can enlarge the smallest lumen diameter and decrease the average area of intimal hyperplasia. This illustrates that the docetaxel-coated stent is less vascular irritative, and docetaxel as a drug used in a stent is more effective than paclitaxel.

It can also be appreciated that the amount of drug released can be adjusted by altering the number of layers in the coating, and the species and quantities of the drug used in each of the layers, so as to satisfy clinical requirements. For example, the stent of Example 7 is coated with a triple-layered coating. In the situation that the drug concentration of the outer layer is zero, the early release of drug may be effectively controlled. The middle layer is added with effective drug of docetaxel in a high concentration, which enables the drug release to reach its climax at the second week. The release of drug of paclitaxel contained in the inner layer can reach its climax at the fourth week and then becomes steady.

In summary, the stent of the present invention may release the drug in a controllable way after being implanted, and the carrier can be degraded and absorbed excellently. The results of the smallest lumen diameter and the average area of intimal hyperplasia also demonstrate that the stent of the present invention can prevent the restenosis and late stage thrombosis safely and effectively, which sufficiently meets the clinical requirements. The drug-coated stent of the present invention has outstanding advantages as follows:

1. The employed asymmetric coating promotes regenerative reparing of vascular endothelium;

2. The multi-layered coating with different drug concentrations in each of layers enables controllable release of drugs so as to satisfy clinical demands.

3. Completing coating at one time with a thin layer can reduce the dosage of carrier and decrease the vascular irritation caused by the carrier.

4. Use of highly effective docetaxel can diminish side effects by reducing the drug dosage and the coating thickness.

5. The drug carrier is made from biodegradable material. Therefore, the degradation cycle and drug releasing rate can be regulated by adjusting the component ratio and molecular weight of the copolymer as carrier, and thus the drug release can be controlled.

INDUSTRIAL APPLICATION

The drug-coated stent of the present invention is a further development of the prior coating technology.

1. Use of highly effective drugs, especially docetaxel, enables a thinnest coating, thus reducing the vascular irritation.

2. The used material for carrier is biodegradable, which has been approved to be applied in vivo, and may disappear immediately after the drug is completely released.

3. The drug release is regulated by altering the coating manner so as to satisfy the clinical requirement for controlled drug release.

4. The employed asymmetric coating promotes regenerative repairing of vascular endothelium.

5. Vascular restenosis may be effectively prevented to reduce occurrence of late thrombosis.

6. The present stent is a drug-coated coronary stent with reasonabe design.

What is claimed is:

1. A coronary stent with asymmetric drug releasing controlled coating, comprising:
   a bare stent; and
   a coating comprising a drug and a carrier,
   wherein the coating is on the outer wall surface alone of the bare stent and comprises an outer layer and an inner layer, and the carrier is a random (lactide-glycolide) copolymer having a molecular weight of 100,000 Da and a polylactide content of 70 mol %, and wherein the drug is docetaxel having a content of 10 μg in the outer layer of the coating and a content of 40 μg in the inner layer of the coating.

2. A coronary stent with asymmetric drug releasing controlled coating, comprising:

a bare stent; and a coating comprising a drug and a carrier, wherein the coating is on the outer wall surface alone of the bare stent and comprises an outer layer, a middle layer, and an inner layer, and the carrier is a random (lactide-glycolide) copolymer having a molecular weight of 80,000 Da and a polylactide content of 75 mol %, and wherein the drug is docetaxel having a content of 15 μg in the outer layer of the coating, rapamycin having a content of 50 μg in the middle layer of the coating and docetaxel having a content of 20 μg in the inner layer of the coating.

3. A coronary stent with asymmetric drug releasing controlled coating, comprising:

a bare stent; and a coating comprising a drug and a carrier, wherein the coating is on the outer wall surface alone of the bare stent and comprises an outer layer, a middle layer, and an inner layer and wherein in the outer layer of the coating, the carrier is a random (lactide-glycolide) copolymer having a molecular weight of 150,000 Da and a polylactide content of 50 mol %, and no drug is included, and in the middle layer of the coating, the carrier is a random (lactide-glycolide) copolymer having a molecular weight of 100,000 and a polylactide content of 70 mol %, and the drug is docetaxel having a content of 55 μg, and in the inner layer of the coating, the carrier is a random (lactide-glycolide) copolymer having a molecular weight of 200,000 and a polylactide content of 80 mol %, and the drug is paclitaxel having a content of 25 μg.

* * * * *